United States Patent [19]
Wachter et al.

[11] 4,130,556
[45] Dec. 19, 1978

[54] CHEMICAL PRODUCTS AND METHODS

[75] Inventors: Michael P. Wachter, Bloomsbury; Ramesh M. Kanojia, Somerville, both of N.J.

[73] Assignee: Ortho Pharmaceutical Corporation, Raritan, N.J.

[21] Appl. No.: 838,527

[22] Filed: Oct. 3, 1977

Related U.S. Application Data

[60] Division of Ser. No. 672,918, Apr. 2, 1976, Pat. No. 4,086,358, and a continuation-in-part of Ser. No. 547,415, Feb. 6, 1975, abandoned.

[51] Int. Cl.$^2$ .................... C07G 17/00; C07D 301/00; A61K 35/78; A61K 31/335
[52] U.S. Cl. ................................. 260/236.5; 260/333; 210/31 C; 424/195; 424/278
[58] Field of Search ............................ 260/236.5, 333; 210/31 C; 424/195, 278

[56] References Cited

U.S. PATENT DOCUMENTS

| | | | |
|---|---|---|---|
| 3,986,952 | 10/1976 | Kanojia et al. | 210/31 C |
| 3,996,132 | 12/1976 | Mateos et al. | 210/31 C |
| 4,006,227 | 2/1977 | Gallegos et al. | 424/195 |

*Primary Examiner*—Donald B. Moyer
*Attorney, Agent, or Firm*—Benjamin F. Lambert

[57] ABSTRACT

Novel compounds obtained from the zoapatle plant and methods of obtaining these compounds from the plant material are described. The novel compounds possess useful activity as central nervous system depressants as well as utero-evacuants.

16 Claims, No Drawings

CHEMICAL PRODUCTS AND METHODS

This is a division of application Ser. No. 672,918, filed Apr. 2, 1976, now U.S. Pat. No. 4,086,358, and a continuation-in-part of application Ser. No. 547,415 filed Feb. 6, 1975 now abandoned.

The present invention relates to pharmacologically active compounds and to processes for isolating the compounds. The compounds which are the subject of this invention can be isolated from the zoapatle plant and possess useful activity as central nervous system depressants and utero-evacuants. The compounds are described by the following formulae:

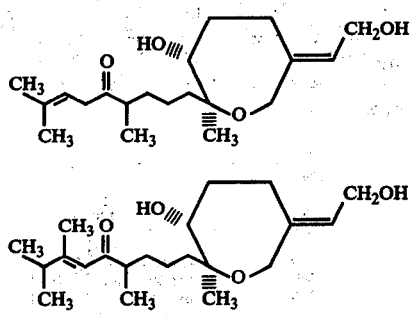

The zoapatle plant is a bush about 2 m. high that grows wild in Mexico. Botanically it is known as *Montanoa tomentosa* according to Cervantes, Fam. Compositae, Tribe Heliantheae; another variety of the species is *Montanoa floribunda*. The plant is described in great detail in *Las Plantas Medicinales de Mexico*, third edition, Ediciones Botas (1944).

The plant has been used for centuries in the form of a "tea" or other crude aqueous preparations primarily as a labor inducer or menses inducer for humans. Its use as a utero-evacuant agent has been documented in the literature, but definitive chemical and pharmacological studies have not been described. By utero-evacuant is meant an agent which causes the uterus of warm blooded animals to contract or expel its contents. Such agents are generally employed to induce menses, expel a hydatiform mole, expel or resorb a fetus, induce abortion or delayed labor and in situations in which the contents of the uterus, such as the fetus or placenta, should be evacuated. Prior to the present invention, a method of isolating and characterizing the active materials from the zoapatle plant has not been described. Nowhere in the art is it reported that the active materials in the zoapatle plant possess activity as central nervous system depressants.

One object of the present invention is to provide a method of isolating and purifying the active materials present in the zoapatle plant.

Another object of the present invention is to provide pharmacologically active materials having definitive pharmacological and chemical properties.

An additional object of the present invention is to provide novel compounds useful as utero-evacuant agents and which also possess useful activity as central nervous system depressants.

These and other objects of this invention will become apparent from the description of the invention provided hereinafter.

The initial extract from which the purified materials are obtained is prepared from the zoapatle plant through a series of extraction and purification steps. In one method dry or fresh leaves of the plant are first suspended in water and the mixture is heated at about 98°–100° C. for several hours. The hot mixture is filtered and the solid residue is washed with hot water. The mixture is filtered a second time and the filtrates are combined. The combined aqueous extracts are extracted several times with an organic solvent. After separation of the aqueous and non-aqueous layers, the organic solvent is removed by techniques known to those skilled in the art. Suitable solvents for the organic extraction include water immiscible aliphatic esters such as ethyl acetate and butyl acetate, aliphatic hydrocarbons such as pentane, hexane and heptane, chlorinated hydrocarbons such as chloroform, carbon tetrachloride and methylene chloride, aromatic hydrocarbons such as benzene and toluene, and water immiscible aliphatic alcohols such as butanol, pentanol, hexanol and the like. The preferred solvent is ethyl acetate. The residue obtained after removal of the organic solvent is then extracted several times with a hot organic solvent such as benzene or toluene. The solvent is again removed and the residue is washed several times with a hot organic solvent, preferably refluxing hexane. As an additional purification step, the residue thus obtained is dissolved in a suitable solvent such as acetone, for example, and stirred with an adsorbent such as charcoal. The residue obtained upon filtration and removal of the solvent is used as the starting material from which the purified materials, which are the subject of this invention, are obtained.

The crude extract obtained by the above procedure is then dissolved in a water immiscible organic solvent, the resulting solution is filtered and the filtrate is washed with an aqueous solution of a mild base, such as, for example, sodium bicarbonate, potassium bicarbonate, sodium carbonate or potassium carbonate, and the like to remove water-soluble and acidic impurities. It is preferred to use a saturated solution of the base. Suitable organic solvents include lower aliphatic ethers such as diethyl ether, di-n-propyl ether, diisopropyl ether, methyl n-butyl ether, ethyl n-butyl ether, and dibutyl ether, lower aliphatic esters such as methyl acetate, ethyl acetate, butyl acetate, ethyl propionate, and other long-chain esters, such as amyl acetate, hexyl acetate, and the like, chlorinated hydrocarbons such as chloroform, carbon tetrachloride and methylene chloride, and aromatic hydrocarbons such as benzene, toluene, xylene and the like.

The organic solvent is removed by techniques known to those skilled in the art, preferably in vacuo, and the semi-pure extract thus obtained is further purified by chromatography over a suitable adsorbent material, such as, for example, silicic acid, silica gel or florisil utilizing a mixture of polar and non-polar solvents as the eluent. The preferred adsorbent is silicic acid. Either neutral or acidic silicic acid may be employed, but it is preferred to employ neutral silicic acid. The material to be chromatographed is preferably first dissolved in a suitable solvent, the preferred solvent is chloroform, added to a column of the adsorbent material packed in a suitable solvent and the column eluted with a mixture of a polar and non-polar solvent. Polar solvents which may be employed include lower alkyl alcohols such as ethanol, methanol, propanol, isopropanol, butanol and the like, lower alkyl esters such as ethyl acetate, butyl acetate and the like, aliphatic ketones, such as acetone, methyl ethyl ketone, methyl isobutyl ketone and the like. Non-polar solvents include chlorinated hydrocarbons such as chloroform, methylene chloride and carbon tetrachloride, and aliphatic hydrocarbon solvents such as pentane, hexane, heptane and the like and aromatic hydrocarbons such as benzene, toluene and the like. The preferred solvent mixture is isopropanol-chloroform. The fractions collected are evaporated to dryness at temperatures ranging from room temperature to about 40° C. The composition of the collected fractions is monitored by thin layer chromatography or gas chromatography. Alternatively, the solution of the crude extract can be chromatographed directly without removal of the solvent. The solution may be concentrated piror to the chromatographic step for ease of handling.

The material obtained as a result of this pruification procedure is a mixture containing at least three major components as evidenced by gas chromatography. The presence of utero-evacuant materials in the mixture is determined through the use of procedures employed for the detection of uterine contractions and interruption of pregnancy in female animals. Interruption of pregnancy in guinea pigs is observed when the mixture is administered in doses ranging from about 50-100 mg./kg. Uterine contractions are detected when about 2.5-5.0 mg./kg. of the mixture are employed.

The fractions containing the pharmacologically active materials are combined and chromatographed through a column of a polymeric gel comprised of organic polymeric materials which swell in organic solvents. Suitable polymeric materials which may be employed include polymers such as vinyl acetate copolymer, cross-linked dextran and polystyrene gels. Suitable solvents include benzene, toluene, tetrahydrofuran, cyclohexane and the like. The preferred polymeric material is vinyl acetate copolymer. The column is eluted with an organic solvent, preferably the one in which the residue is dissolved. The preferred solvent is benzene. A number of fractions are generally collected and the composition of the fractions is followed by gas chromatography or thin layer chromatography. As a result of the above procedure, two chemically distinct compounds are obtained as evidenced by gas chromatography and spectral analyses. If desired, minor impurities can be removed from the purified compounds by further chromatography on adsorbents, such as, for example, silicic acid or florisil. The column is eluted with an organic solvent or a mixture of solvents, chloroform-isopropanol being the solvent mixture of choice, and the composition of the fractions collected is followed by thin layer chromatography.

The purified compounds are effective in inducing uterine contractions when administered in doses ranging from about 1.0 mg. to about 85 mg./kg. The purified compounds are effective in interrupting pregnancy at dosage levels between about 15 to about 100 mg./kg. The preferred dosage range is from about 20-85 mg./kg. As central nervous system depressants, the compounds are active in doses as low as 3.7 mg./kg. The actual dosage employed will depend upon the species of animal to which the compound is administered. The compounds can be administered in formulations prepared according to acceptable pharmaceutical practices. Suitable formulations would include solutions, suspensions and solid dosage forms in pharmaceutically acceptable carriers. They can be administered perorally or intravenously or in any conventional manner in accordance with acceptable pharmaceutical practices.

The following describes the invention in greater particularity and is intended to be a way of illustrating but not limiting the invention.

EXAMPLE I

The crude extract used as the starting material (50 g.) is dissolved in ether (5l.) and the resulting solution is filtered and washed with saturated sodium bicarbonate solution (500 ml.). The ether is dried over anhydrous sodium sulfate, filtered and concentrated to dryness to afford a light yellow oil (44.6 g.). This oil is then dissolved in chloroform (400 ml.) and the solution added to a column (4 in. × 4 ft.) of 2.5 kg. of neutral silicic acid packed in chloroform. The column is eluted with chloroform, chloroform-isopropanol mixtures, and 110 fractions are collected. The fractions are evaporated to dryness in vacuo at a temperature below 40° C. The column is eluted as follows:

| Fraction | Volume/Fraction (ml.) | Eluent |
|---|---|---|
| 1-7 | 650 | CHCl₃ |
| 8-30 | 500 | isopropanol:CHCl₃ (1:41.7) |
| 31-60 | 500 | isopropanol:CHCl₃ (1:33.3) |
| 61-105 | 500 | isopropanol:CHCl₃ (1:28.6) |
| 106-110 | 500 | isopropanol:CHCl₃ (1:25) |

The composition of the fractions is monitored by thin layer chromatography [silica gel, isopropanol-chloroform (1:12.5)] and by gas chromatography — 3% OV17 [methyl silicone-phenyl silicone (1:1)] column using a prgrammed run (150°-250°). Fractions Nos. 78-84 are combined and the solvent removed in vacuo to afford an oily residue (5.1 g.) which contains at least three major components as indicated by gas chromatography.

A portion of the residue (3.2 g.) is then dissolved in benzene (50 ml.) and the solution added to a column (4 in. × 35 in.) packed with 2 kg. of OR-PVA Merck-O-Gel 2000* prepared in benzene. The column is eluted with benzene and a total of 47 fractions is collected. Thin layer chromatography and gas chromatography are used to monitor the composition of the fractions.

*A vinyl acetate copolymer which swells in organic solvents, produced by E. M. Merck, Inc. and sold under the trademark EM Gel® Type OR-PVA.

| Fractions | Volume/Fraction (ml.) |
|---|---|
| 1-7 | 1000 |
| 8-45 | 300 |
| 46-47 | 1000 |

Fractions 23-33 contain 1.73 g. (54%) of the applied material.

(A) Fractions 24-25 are evaporated to give a compound (Formula II) as an oil (0.251 g.) having the following spectral characteristics:
I.R. (Neat)μ: 2.90, 5.96 and 6.21
N.M.R. TMS/CDCl₃ δ: 6.11 (broad s, 1,

5.48 (m, 1, C=C$\underline{H}$—CH₂OH); 4.19 (d, 2, C=CH—C$\underline{H}$₂OH);

4.13 (s, 2, C—O—CH₂—C̸=); 3.56 [broad t, 1, —ĊH(OH)];

2.10 (d, 3, H₃C—C̸=C); 1.13 (s, 3, C—O—Ċ—CH₃);

1.07 [d, 6, C=Ċ—CH(CH₃)₂]

Mass Spec [m/e]: 334 [M-18], 225, 140, 111, 95, 81, 69
U.V. — λ max (EtOH): ~ 239 nm [ε=8500]
Chemical Ionization: M⁺ + H = 353; M.W. = 352

(B) Fraction 31 is evaporated to give a compound (Formula I) as an oil (0.326 g.) having the following spectral characteristics:

I.R. (Neat) μ: 2.91 and 5.88
N.M.R. TMS/CDCl₃ δ: 5.41

$$m, 2, \text{>}C=CH-CH_2OH \text{ and } \text{>}C=CH-CH_2-\overset{O}{\overset{\|}{C}}-);$$

4.20 (d, 2, C=CH—CH₂OH); 4.15 (s, 2, C—O—CH₂—Ċ=);

3.58 [broad t, 1, >CH(OH)]; 3.18 (d, 2, C=CH —CH₂—C̈—);

1.71 [d, 6, C=C—(CH₃)₂]; 1.15 (s, 3, C—O—Ċ—CH₃)

Mass spec [m/e]: 320 [M-18], 251, 233, 221, 171, 143, 141, 137, 125, 113, 97, 95, 81, 69
Chemical Ionization: M⁺ + H = 339; M.W. = 338

The following general procedure is a standard procedure employed to detect uterine contractions in female animals.

PROCEDURE I

Mature female New Zealand rabbits are anesthetized with sodium pentobarbital and ovariectomized. Following a recovery period of 1 week, the rabbits are treated with 5 μg./day s.c. of 17β-estradiol for 6 consective days, followed by treatment with 1.0 mg./day s.c. of progesterone for 7 consecutive days. The uterus and oviducts of the rabbits are perfused 72 hours after the last dose of progesterone according to the method of Heilman, et al., (Fertil. Steril. 23:221-229) with slight modifications. The oviduct and uterus are perfused at a rate of 53 μl./min. The uterus is perfused with a tube extending 1.0 cm. into the lumen of the uterus from the oviducal end. The uterus is ligated at the utero-tubal junction. Another cannula is inserted 1.0 cm. into the uterus through a small incision in the vagina in order to collect perfusate. The material to be tested is administered i.v. through the jugular vein in a vehicle that contains polyethylene glycol 200, polyethylene glycol 400, ethanol and a phosphate buffer. The cannula is attached to a P23-Dc Stathan transducer which in turn is coupled to a Grass Model 5 polygraph and the uterine contractility measured.

Intravenous adminstration of the compound obtained from Fraction 31 is effective in inducing uterine contractions and relaxing the oviduct in 72-hour progesterone withdrawn rabbits in a dose range of 1.0–4.0 mg./kg. The compound obtained from Fractions 24–25 is effective when administered in a dose range of from 25–40 mg./kg.

The following general procedure is a standard procedure employed to detect interruption of pregnancy after implantation has occurred.

PROCEDURE II

Mature, Hartley strain, female guinea pigs are continuously cohabited (monogamously) with males until a vaginal plug (copulation plug) is found in the cage. This time is considered to be day 1 of gestation. Groups of 5-6 females are given test materials intraperitoneally in the vehicle described in Procedure I on day 22 of gestation. The pigs are sacrificed between the 25th and 45th day of gestation and examined for evidence of resorption or abortion.

Intraperitoneal administration of the material obtained from Fraction 31 is effective in interrupting pregnancy when administered in a dose range from 25-85 mg./kg.

The following general procedure is a standard procedure employed to determine CNS activity.

PROCEDURE III

Male CF1, Charles River mice weighing 25–30 grams (4/group) were dosed once intraperitoneally with the compound of Formula I (3.7 mg./kg.) suspended by insonation in equal parts of sesame oil and water to which had been added a drop of Tween 80.

The animals were weighed and surface (paw) and core (rectal) temperature was determined. The mice were then dosed and observed for behavioral changes indicative of neuropharmacologic action. Observations were made of the time of onset of drug action, the time at which the peak effect occurred, and the duration of action. Mice were observed continuously for a period of 60 minutes.

At the time of peak effect following treatment, the mice were subjected to a series of tests designed to help evaluate behavioral changes. Temperature was recorded 30 minutes post-treatment.

(1) The awareness and alertness of the animal was tested by observing their reaction to a hand-held probe randomly moved in their vicinity.
(2) Reactivity was tested by placing each mouse in the center of the test arena to see if he moved purposefully.
(3) Startle response was tested by a finger snap.
(4) Corneal and pineal reflexes were induced with a thin wire probe.
(5) Withdrawal reflex was tested by gentle adduction of a hind limb.
(6) Touch reflex was examined by stroking the animal from thorax to the base of its tail.
(7) Response to pain was studied following pressure applied to the base of the tail with a pair of forceps.
(8) Visual placing was assessed by slowly lowering the tail-held mouse to a table top to see if he extended his forelimbs prior to contact with the table.
(9) Spatial orientation was observed by placing the mouse near the table edge and evaluating his response to this positional stimulus.
(10) Muscle coordination was examined by observing the ability of the mouse to walk a string tightly stretched between two vertical posts.

(11) An inclined screen was used to assess grip strength, catatonia muscle relaxation, etc.

(12) Passivity was assayed by positioning the animal abnormally (on his back) to determine the extent of his awareness and to observe his attempts to recover from the abnormal position.

(13) Body and limb tone were observed by the subjective "feel" of the mouse while being hand-held.

(14) Pupil size was observed under a moderately intense light.

(15) Righting reflex was tested by flipping the mouse end-over-end 2–3 times to see if he was capable of recovering balance in order to land on his feet.

(16) During the course of the study, observations were also made of hypersensitivity, stereotypic behavior, depression, irritability, vocalization, straub tail, arched back, tremors, twitches, convulsions, ataxia, paralysis, abnormal gait, head drop, aggressiveness, fearfulness, cluster, palpebral opening, exophthalmus, eye opacity, increased or decreased lacrymation, salivation, urination or defecation, piloerection, changes in skin color, changes in respiratory rate, and writhing.

(17) Mice were observed periodically for 48 hours, and the number dead during that time was used to compute the LD50.

This study indicates that the compound of Formula I is a CNS depressant with muscle relaxing properties when administered in doses as low as 3.7 mg./kg.

PREPARATION OF STARTING MATERIAL (CRUDE EXTRACT)

Ten kg. of dried or fresh leaves from the zoapatle plant and 30 gallons of water are added to a 100 gallon steam-jacketed stainless steel tank. The mixture is heated at 98°–100° C. for 2.5 hours with periodic stirring. The hot mixture is filtered through gauze to afford a clear dark tea, about 25 gallons in volume. The solid residue in the tank is washed with 4 gallons of hot water, filtered, and the filtrate combined with the tea obtained above. The combined aqueous extracts are extracted with 30 gallons of ethyl acetate. The mixture is stirred vigorously and allowed to settle. The top frothy layer is siphoned off to break the emulsion, and as much ethyl acetate separated as possible. Another 20 gallons of ethyl acetate are added to the mixture and the above process repeated. The combined ethyl acetate extracts are evaporated at 50° C. under vacuum. The residue is extracted with three portions of hot (75°–80°) benzene (10 liters total). The benzene extracts are evaporated at 50° C. under vacuum and the residue is washed three times with a total of 8 liters of refluxing hexane. The hexane-washed residue is dissolved in 2 liters of acetone, 10 g. of Nuchar is added, and the mixture is stirred 1 hour at room temperature. The charcoal is removed by filtration, and the filtrate evaporated by distillation at 30° C. under vacuum to afford 69 g. of crude extract. This crude extract is used as the starting material in Example 1.

What is claimed is:

1. The method of purifying crude extracts containing biologically active materials obtained from the zoapatle plant selected from the species consisting of *Montanoa tomentosa* and *Montanoa floribunda* which comprises the steps of:
dissolving the crude extract in a water-immiscible organic solvent, washing the resulting solution with an aqueous solution of a mild base and separating the organic phase from the aqueous phase, chromatographing the solution through a column of adsorbent material, eluting the column with a mixture of a polar and a non-polar solvent, combining the fractions containing biologically active materials and removing the solvent therefrom, dissolving the residue in a water-immiscible organic solvent, chromatographing the solution through a column of an organic polymeric gel, eluting the column with a non-polar organic solvent and collecting the fractions containing biologically active materials.

2. The method of claim 1 wherein the species of zoapatle plant is *Montanoa tomentosa*.

3. The method of claim 1 wherein the water-immiscible organic solvent is selected from an aromatic hydrocarbon, a chlorinated hydrocarbon or an aliphatic ether.

4. The method of claim 1 wherein the organic solvent is selected from ether, chloroform or benzene.

5. The method of claim 1 wherein the adsorbent material is selected from silicic acid, silica gel and florisil.

6. The method of claim 1 wherein the mixture of polar and non-polar solvents comprises chloroform and isopropanol.

7. The method of claim 1 wherein the polymeric gel is a vinyl acetate copolymer.

8. The method of claim 1 wherein the non-polar solvent is benzene.

9. The method of claim 1 wherein the mild base is sodium bicarbonate.

10. The method of purifying extracts containing biologically active materials obtained from a species of the zoapatle plant selected from *Montanoa tomentosa* and *Montanoa floribunda* which comprises the steps of:
dissolving the crude extract in a lower aliphatic ether, washing the solution with an aqueous solution of a mild base and separating the organic phase from the aqueous phase, chromatographing the solution through a column of adsorbent material, eluting the column with a mixture of a polar and a non-polar solvent, combining the fractions containing the biologically active materials and removing the solvent therefrom, dissolving the residue in an aromatic hydrocarbon, chromatographing the solution through a column of a polymeric gel, eluting the column with an aromatic hydrocarbon and collecting the fractions containing the biologically active materials.

11. The method of claim 10 wherein the zoapatle plant is *Montanoa tomentosa*.

12. The method of claim 10 wherein the aliphatic ether is diethyl ether.

13. The method of claim 10 wherein the adsorbent material is silicic acid or silica gel.

14. The method of claim 10 wherein the mixture of polar and non-polar solvents comprises chloroform and isopropanol.

15. The method of claim 10 wherein the aromatic hydrocarbon is benzene.

16. The method of claim 10 wherein the polymeric gel is vinyl acetate copolymer.

* * * * *

UNITED STATES PATENT AND TRADEMARK OFFICE
CERTIFICATE OF CORRECTION

PATENT NO. : 4,130,556　　　　　　　　　　　　　Page 1 of 2
DATED : December 19, 1978
INVENTOR(S) : Michael P. Wachter, Ramesh M. Kanojia It is certified that error appears in the above-identified patent and that said Letters Patent are hereby corrected as shown below:

At Column 3, Line 17, "prufication" should be -- purification --.
At Column 4, Line 34, "prgrammed" should be -- programmed --.
At Column 4, Lines 63-65, spectral characteristics, $$\text{"} \quad -\underset{\text{"}}{\overset{\overset{O}{\text{"}}}{C}}-CH=C); \quad \text{"} \quad \text{should be} \quad -- \quad -\underset{\text{"}}{\overset{\overset{O}{\text{"}}}{C}}-\underline{C}H=C); \quad --.$$

At Column 5, Lines 3-4, spectral characteristics,
" 4.13(s,2, C-O-CH$_2$-C=); 3.56[broad t,1,-CH(OH)];" should be
-- 4.13(s,2, C-O-C$\underline{H}_2$-C=); 3.56[broad t,1,-C$\underline{H}$(OH)]; --.

At Column 5, Lines 5-7, spectral characteristics,
" 2.10(d,3,H$_3$C-C=C); 1.13(s,3,C-O-C-CH$_3$); " should be
-- 2.10(d,3,$\underline{H}_3$C-C=C); 1.13(s,3,C-O-C-C$\underline{H}_3$); --.

At Column 5, Lines 9-10, spectral characteristics,
" 1.07[d,6,C=C-CH(CH$_3$)$_2$] " should be
-- 1.07[d,6,C=C-CH(C$\underline{H}_3$)$_2$] --.

At Column 5, Lines 22-24, spectral characteristics,
" m,2, >C=CH-CH$_2$OH and >C=CH-CH$_2$-C(=O)-); " should be
-- m,2, >C=C$\underline{H}$-CH$_2$OH and >C=C$\underline{H}$-CH$_2$-C(=O)-); --.

UNITED STATES PATENT AND TRADEMARK OFFICE
CERTIFICATE OF CORRECTION

PATENT NO. : 4,130,556
DATED : December 19, 1978
INVENTOR(S) : Michael P. Wachter, Ramesh M. Kanojia It is certified that error appears in the above-identified patent and that said Letters Patent are hereby corrected as shown below:

At Column 5, Lines 25-26, spectral characteristics,

"4.20(d,2,C=CH-CH$_2$OH); 4.15(s,2,C-O-CH$_2$-C=);" should be

--4.20(d,2,C=CH-C$\underline{H}_2$OH); 4.15(s,2,C-O-C$\underline{H}_2$-C=); --.

At Column 5, Lines 28-30, spectral characteristics,

"3.58[broad t,1, >CH(OH)]; 3.18(d,2,C=CH-CH$_2$-C(=O)-); should be

--3.58[broad t,1, >C$\underline{H}$(OH)]; 3.18(d,2,C=CH-C$\underline{H}_2$-C(=O)-); --.

At Column 5, Lines 31-33, spectral characteristics,

"1.71[d,6,C=C-(CH$_3$)$_2$]; 1.15(s,3,C-O-C-CH$_3$)" should be

--1.71[d,6,C=C-(C$\underline{H}_3$)$_2$]; 1.15(s,3,C-O-C-C$\underline{H}_3$) --.

Signed and Sealed this

Seventeenth Day of April 1979

[SEAL]

Attest:

RUTH C. MASON
Attesting Officer

DONALD W. BANNER
Commissioner of Patents and Trademarks